United States Patent
Dodge, II et al.

[11] Patent Number: 5,994,615
[45] Date of Patent: *Nov. 30, 1999

[54] HIGHLY EFFICIENT SURGE MATERIAL FOR ABSORBENT ARTICLE

[75] Inventors: Richard Norris Dodge, II, Appleton, Wis.; Clifford Jackson Ellis, Woodstock, Ga.; Connie Lynn Hetzler, Alpharetta, Ga.; Sylvia Bandy Little, Marietta, Ga.; Tamara Lee Mace, Doraville, Ga.; Lawrence Howell Sawyer, Roswell, Ga.; Hoa La Wilhelm, Appleton, Wis.

[73] Assignee: Kimberly-Clark Worldwide, Inc., Neenah, Wis.

[*] Notice: This patent is subject to a terminal disclaimer.

[21] Appl. No.: 09/212,934

[22] Filed: Dec. 16, 1998

Related U.S. Application Data

[62] Division of application No. 08/755,514, Nov. 22, 1996, Pat. No. 5,879,343.

[51] Int. Cl.⁶ .............................. A61F 13/15; B32B 7/02
[52] U.S. Cl. ........................ 604/378; 442/416; 442/212; 442/218
[58] Field of Search ............................. 604/378; 442/364, 442/416, 212, 218

[56] References Cited

U.S. PATENT DOCUMENTS

| | | | |
|---|---|---|---|
| H1377 | 11/1994 | Perry | 604/385.1 |
| H1511 | 12/1995 | Chappell et al. | 604/383 |
| 3,338,992 | 8/1967 | Kinney | 364/24 |
| 3,341,394 | 9/1967 | Kinney | 161/72 |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 4,100,324 | 7/1978 | Anderson et al. | 428/288 |
| 4,340,563 | 7/1982 | Appel et al. | 264/518 |
| 4,397,644 | 8/1983 | Matthews et al. | 604/378 |
| 4,413,032 | 11/1983 | Hartmann et al. | 428/288 |
| 4,480,000 | 10/1984 | Watanabe et al. | 428/284 |
| 4,500,315 | 2/1985 | Pieniak et al. | 604/379 |
| 4,531,945 | 7/1985 | Allison | 604/378 |
| 4,537,590 | 8/1985 | Pieniak et al. | 604/379 |

(List continued on next page.)

FOREIGN PATENT DOCUMENTS

| | | | |
|---|---|---|---|
| 2147685 | 2/1996 | Canada | A61F 13/54 |
| 0 539 703 | 5/1993 | European Pat. Off. | A61F 13/15 |
| 0 640 330 | 3/1995 | European Pat. Off. | A61F 13/46 |
| 0 670 154 | 9/1995 | European Pat. Off. | A61F 13/15 |
| 0 719 530 | 7/1996 | European Pat. Off. | A61F 13/15 |
| 8164160 | 6/1996 | Japan | A61F 13/15 |
| 8164163 | 6/1996 | Japan | A61F 13/46 |

(List continued on next page.)

OTHER PUBLICATIONS

Research Disclosure 37421, "Thermally Bonded Absorbent Structures Having Discrete, Stepped Desity Zones in the Z–Dimension," Jun. 1995, Inventor—Anonymous, Class/Subclass: 156/298.

*Polymer Blends and Composites,* John A. Manson and Leslie H. Sperling, copyright 1976, Plenum Press, ISBN–0–306–30831–2, pp. 273–277.

Article by R.W. Hoyland and R. Field in *Paper Technology and Industry,* Dec. 1976, pp. 291–299 and *Porous Media Fluid Transport and Pore Structure,* F.A.L. Dullien, 1979, Academic Press, Inc. ISBN 0–12–223650–5.

*Primary Examiner*—Mark O. Polutta
*Attorney, Agent, or Firm*—James B. Robinson

[57] ABSTRACT

There is provided a surge material for personal care products which is a wettable web of fibers of 30 microns in diameter or less where the web has a permeability between about 250 and 1500 Darcys, a capillary tension between about 1.5 and 5 cm, and which maintains that permeability and capillary tension over the life of the web. Its preferred that the web have a density between about 0.02 g/cc to about 0.07 g/cc.

16 Claims, 4 Drawing Sheets

U.S. PATENT DOCUMENTS

| | | | |
|---|---|---|---|
| 4,540,414 | 9/1985 | Wishman | 604/378 |
| 4,573,988 | 3/1986 | Pieniak et al. | 604/379 |
| 4,578,070 | 3/1986 | Hoitman | 604/378 |
| 4,636,209 | 1/1987 | Lassen | 604/378 |
| 4,637,819 | 1/1987 | Quellette et al. | 604/369 |
| 4,650,479 | 3/1987 | Insley | 604/358 |
| 4,670,011 | 6/1987 | Mesek | 604/378 |
| 4,673,402 | 6/1987 | Weisman et al. | 604/368 |
| 4,681,577 | 7/1987 | Stern et al. | 604/378 |
| 4,684,914 | 8/1987 | Holtman | 604/368 |
| 4,699,619 | 10/1987 | Bernardin | 604/378 |
| 4,723,953 | 2/1988 | Rosenbaum et al. | 604/369 |
| 4,755,178 | 7/1988 | Insley et al. | 604/367 |
| 4,798,603 | 1/1989 | Meyer et al. | 604/378 |
| 4,818,464 | 4/1989 | Lau | 264/510 |
| 4,834,735 | 5/1989 | Alemany et al. | 604/368 |
| 4,842,594 | 6/1989 | Ness | 604/368 |
| 4,880,419 | 11/1989 | Ness | 604/368 |
| 4,892,534 | 1/1990 | Datta et al. | 604/370 |
| 4,904,249 | 2/1990 | Miller et al. | 604/378 |
| 4,908,026 | 3/1990 | Sukiennik et al. | 604/378 |
| 4,935,022 | 6/1990 | Lash et al. | 604/368 |
| 4,938,756 | 7/1990 | Salek | 604/368 |
| 4,950,264 | 8/1990 | Osborn, III | 604/385.1 |
| 4,988,344 | 1/1991 | Reising et al. | 604/368 |
| 4,988,345 | 1/1991 | Reising | 604/368 |
| 4,994,037 | 2/1991 | Bernardin | 604/368 |
| 5,009,653 | 4/1991 | Osborn, III | 604/385.1 |
| 5,030,229 | 7/1991 | Yang | 604/385.1 |
| 5,037,409 | 8/1991 | Chen et al. | 604/358 |
| 5,043,206 | 8/1991 | Ternström | 428/218 |
| 5,047,023 | 9/1991 | Berg | 604/368 |
| 5,057,368 | 10/1991 | Largman et al. | 428/397 |
| 5,062,839 | 11/1991 | Anderson | 604/385.1 |
| 5,069,970 | 12/1991 | Largman et al. | 428/373 |
| 5,108,820 | 4/1992 | Kaneko et al. | 428/198 |
| 5,108,827 | 4/1992 | Gessner | 428/219 |
| 5,124,197 | 6/1992 | Bernardin et al. | 428/284 |
| 5,134,007 | 7/1992 | Reising et al. | 428/78 |
| 5,147,345 | 9/1992 | Young et al. | 604/378 |
| 5,171,391 | 12/1992 | Chmielewski et al. | 156/229 |
| 5,176,668 | 1/1993 | Bernardin | 604/368 |
| 5,188,624 | 2/1993 | Young, Sr. et al. | 604/378 |
| 5,192,606 | 3/1993 | Proxmire et al. | 428/284 |
| 5,200,248 | 4/1993 | Thompson et al. | 428/131 |
| 5,217,445 | 6/1993 | Young et al. | 604/381 |
| 5,236,427 | 8/1993 | Hamajima et al. | 604/378 |
| 5,242,435 | 9/1993 | Murji et al. | 604/374 |
| 5,248,309 | 9/1993 | Serbiak et al. | 604/368 |
| 5,257,982 | 11/1993 | Cohen et al. | 604/378 |
| 5,277,976 | 1/1994 | Hogle et al. | 428/397 |
| 5,281,207 | 1/1994 | Chmielewski et al. | 604/378 |
| 5,281,208 | 1/1994 | Thompson et al. | 604/378 |
| 5,294,478 | 3/1994 | Wanek et al. | 428/218 |
| 5,300,054 | 4/1994 | Feist et al. | 604/378 |
| 5,304,161 | 4/1994 | Noel et al. | 604/378 |
| 5,318,554 | 6/1994 | Young et al. | 604/378 |
| 5,330,457 | 7/1994 | Cohen | 604/378 |
| 5,334,176 | 8/1994 | Buenger et al. | 604/367 |
| 5,334,177 | 8/1994 | Cohen | 604/378 |
| 5,336,552 | 8/1994 | Strack et al. | 428/224 |
| 5,342,334 | 8/1994 | Thompson et al. | 604/366 |
| 5,342,336 | 8/1994 | Meirowitz et al. | 604/378 |
| 5,348,547 | 9/1994 | Payne et al. | 604/378 |
| 5,350,370 | 9/1994 | Jackson et al. | 604/367 |
| 5,356,405 | 10/1994 | Thompson et al. | 604/384 |
| 5,360,420 | 11/1994 | Cook et al. | 604/378 |
| 5,364,382 | 11/1994 | Latimer et al. | 604/378 |
| 5,366,451 | 11/1994 | Levesque | 604/378 |
| 5,368,926 | 11/1994 | Thompson et al. | 428/284 |
| 5,382,245 | 1/1995 | Thompson et al. | 604/367 |
| 5,382,400 | 1/1995 | Pike et al. | 264/168 |
| 5,401,267 | 3/1995 | Couture-Dorschner | 604/384 |
| 5,418,045 | 5/1995 | Pike et al. | 428/198 |
| 5,423,787 | 6/1995 | Kjellberg | 604/368 |
| 5,429,629 | 7/1995 | Latimer et al. | 604/378 |
| 5,439,458 | 8/1995 | Noel et al. | 604/378 |
| 5,456,982 | 10/1995 | Hansen et al. | 428/370 |
| 5,460,622 | 10/1995 | Dragoo et al. | 604/378 |
| 5,466,410 | 11/1995 | Hills | 264/172.11 |
| 5,466,513 | 11/1995 | Wanek et al. | 428/218 |
| 5,486,166 | 1/1996 | Bishop et al. | 604/366 |
| 5,486,167 | 1/1996 | Dragoo et al. | 604/384 |
| 5,487,736 | 1/1996 | Van Phan | 604/368 |
| 5,490,846 | 2/1996 | Ellis et al. | 604/366 |
| 5,505,719 | 4/1996 | Cohen et al. | 604/372 |
| 5,509,915 | 4/1996 | Hanson et al. | 604/378 |
| 5,514,105 | 5/1996 | Goodman, Jr. et al. | 604/370 |
| 5,514,120 | 5/1996 | Johnston et al. | 604/378 |
| 5,525,407 | 6/1996 | Yang | 428/218 |
| 5,527,300 | 6/1996 | Sauer | 604/378 |
| 5,531,728 | 7/1996 | Lash | 604/378 |
| 5,536,264 | 7/1996 | Hsueh et al. | 604/368 |
| 5,540,979 | 7/1996 | Yahiaoui et al. | 428/212 |
| 5,549,589 | 8/1996 | Horney et al. | 604/366 |
| 5,556,392 | 9/1996 | Koczab | 604/378 |
| 5,562,646 | 10/1996 | Goldman et al. | 604/368 |
| 5,562,650 | 10/1996 | Everett et al. | 604/378 |
| 5,569,226 | 10/1996 | Cohen et al. | 604/378 |
| 5,599,335 | 2/1997 | Goldman et al. | 604/368 |
| 5,601,545 | 2/1997 | Glaug et al. | 604/385.2 |
| 5,607,414 | 3/1997 | Richards et al. | 604/378 |
| 5,611,981 | 3/1997 | Phillips et al. | 264/130 |
| 5,628,736 | 5/1997 | Thompson | 604/366 |
| 5,641,441 | 6/1997 | Yang | 264/113 |
| 5,643,238 | 7/1997 | Baker | 604/368 |
| 5,647,862 | 7/1997 | Osborn, III et al. | 604/378 |
| 5,649,916 | 7/1997 | DiPalma et al. | 604/378 |
| 5,658,268 | 8/1997 | Johns et al. | 604/361 |
| 5,665,082 | 9/1997 | Boulanger | 604/365 |
| 5,879,343 | 3/1999 | Dodge et al. | 604/378 |

FOREIGN PATENT DOCUMENTS

| | | | |
|---|---|---|---|
| 8299385 | 11/1996 | Japan | A61F 13/15 |
| 8317939 | 12/1996 | Japan | A61B 19/08 |
| 9000562 | 1/1997 | Japan | A61F 13/15 |
| 9117471 | 5/1997 | Japan | A61F 13/54 |
| 2 269 109 | 2/1994 | United Kingdom | A61F 13/15 |
| 2 287 041 | 9/1995 | United Kingdom | D04H 1/54 |
| 2 295 321 | 5/1996 | United Kingdom | A61F 13/46 |
| 90/12130 | 10/1990 | WIPO | D01D 5/253 |
| 91/11978 | 8/1991 | WIPO | A61F 13/46 |
| 93/15702 | 8/1993 | WIPO | A61F 13/50 |
| 94/29506 | 12/1994 | WIPO | D04H 13/00 |
| 95/00183 | 1/1995 | WIPO | A61L 15/60 |
| 95/01147 | 1/1995 | WIPO | A61F 13/15 |
| 95 16422 | 6/1995 | WIPO | A61F 13/15 |
| 95/25495 | 9/1995 | WIPO | A61F 13/15 |
| 95/35081 | 12/1995 | WIPO | A61F 13/15 |
| 96/01608 | 1/1996 | WIPO | A61F 13/15 |
| 96/03947 | 2/1996 | WIPO | A61F 13/15 |
| 96/12460 | 5/1996 | WIPO | A61F 13/15 |
| 96/20667 | 7/1996 | WIPO | A61F 13/15 |
| 96/41045 | 12/1996 | WIPO | D04H 1/46 |
| 97/11660 | 4/1997 | WIPO | A61F 13/15 |
| 97/13909 | 4/1997 | WIPO | . |
| 9723182 | 7/1997 | WIPO | A61F 13/15 |

HIGHLY EFFICIENT SURGE MATERIAL FOR ABSORBENT ARTICLE

This application is a divisional of application Ser. No. 08/755,514 entitled "Highly Efficient Surge Material for Absorbent Articles" and filed in the U.S. Patent and Trademark Office on Nov. 22, 1996 now U.S. Pat. No. 5,879,343. The entirety of this application is hereby incorporated by reference.

FIELD OF THE INVENTION

This invention relates to absorbent articles particularly absorbent structures which are useful in personal care products such as disposable diapers, incontinence guards, child care training pants, or sanitary napkins. More particularly, the invention relates to absorbent articles which have a portion designed for rapid intake, temporary liquid control, and subsequent release of repeated liquid surges to the remainder of the article.

BACKGROUND OF THE INVENTION

Personal care products are absorbent articles including diapers, training pants, feminine hygiene products such as sanitary napkins, incontinence devices and the like. These products are designed to absorb and contain body exudates and are generally single-use or disposable items which are discarded after a relatively short period of use—usually a period of hours—and are not intended to be washed and reused. Such products usually are placed against or in proximity to the wearers body to absorb and contain various exudates discharged from the body. All of these products typically include a liquid permeable bodyside liner or cover, a liquid impermeable outer cover or backsheet, and an absorbent structure disposed between the bodyside liner and outer cover. The absorbent structure may include a surge layer subjacent to and in liquid communicating contact with the bodyside liner, and an absorbent core often formed of a blend or mixture cellulosic pulp fluff fibers and absorbent gelling particles subjacent to and in liquid communicating contact with the surge layer.

Desirably, personal absorbent articles exhibit low leakage from the product and a dry feel for the wearer. It has been found that urination can occur at rates as high as 15 to 20 milliliters per second and at velocities as high as 280 centimeters per second and that an absorbent garment, such as a diaper, may fail by leaking from the leg or front or back waist areas. The inability of the absorbent product to rapidly uptake liquid can also result in excessive pooling of liquid on the body-facing surface of the bodyside liner before the liquid is taken up by the absorbent structure. Such pooled liquid can wet the wearer's skin and can leak from leg or waist openings of the absorbent article, causing discomfort, potential skin health problems, as well as soiling of the outer clothing or bedding of the wearer. Leakage and pooling can result from a variety of performance deficiencies in the design of the product, or individual materials within the product. One cause of such problems is an insufficient rate of liquid intake into the absorbent core, which functions to absorb and retain body exudates. The liquid intake of a given absorbent product, therefore, and particularly the bodyside liner and surge materials used in absorbent product, must attempt to meet or exceed the expected liquid delivery rates into the absorbent product. An insufficient intake rate becomes even more detrimental to product performance on second, third, or fourth liquid surges. In addition, leakage may occur due to poor wet product fit that results when multiple insults are stored in the target location and cause sagging and drooping from the wet, heavy retention material structure.

Various approaches have been taken to reduce or eliminate leakage from personal care absorbent articles. For example, physical barriers, such as elasticized leg openings and elasticized containment flaps, have been incorporated into such absorbent products. The amount and configuration of absorbent material in the zone of the absorbent structure in which liquid surges typically occur (sometimes referred to as a target zone) also have been modified.

Other approaches to improving overall liquid intake of absorbent articles have focused on the bodyside liner and its capacity to rapidly pass liquid to the absorbent structure of the absorbent article. Nonwoven materials, including bonded carded webs and spunbond webs, have been widely used as bodyside liners. Such nonwoven materials generally are intended to be sufficiently open and/or porous to allow liquid to pass through rapidly, while also functioning to keep the wearer's skin separate from the wetted absorbent underlying the liner. Attempts to improve the liquid intake of liner materials have included, for example, aperturing the liner material, treating the fibers forming the liner material with surfactants to enhance the wettability of the liner, and altering the durability of such surfactants.

Yet another approach has been to introduce one or more additional layers of material, typically between the bodyside liner and absorbent core, to enhance the liquid intake performance of the absorbent product and to provide separation between the absorbent core and the bodyside liner adjacent the wearer's skin. One such additional layer, commonly referred to as a surge layer, can suitably be formed of thick, lofty nonwoven materials. Surge layers, particularly high loft, high bulk, compression resistant fibrous structures, provide a temporary retention or absorption function for liquid not yet absorbed into the absorbent core, which tends to reduce fluid flowback or wetback from the absorbent core to the liner.

Despite these improvements, the need exists for further improvement in the liquid intake performance of liner materials employed in absorbent articles. In particular, there is a need for liner materials that can rapidly intake and then control a large portion of a liquid insult for extended times between insults. This improved handling is critical for narrow crotch absorbent product designs that utilize less retention storage material in the target region and incorporate distribution features that remove fluid for storage in remote locations in order to alleviate fit problems as a means to reduce leakage. The present invention provides a highly efficient surge material that provides for such improved liquid intake and holding when used in absorbent articles.

SUMMARY OF THE INVENTION

The objects of this invention are achieved by a surge material for personal care products which is a wettable web of fibers of at most 30 microns in diameter where the web has a permeability between about 250 and 1500 Darcys, a capillary tension between about 1.5 and 5 cm, and which maintains that permeability and capillary tension over the life of the web. Its preferred that the web have a density between about 0.02 g/cc to about 0.07 g/cc. Such a surge material is well suited for use in narrow crotch personal care products, for example, diapers having a crotch of at most 7.6 cm in width.

DEFINITIONS

Figure 1:
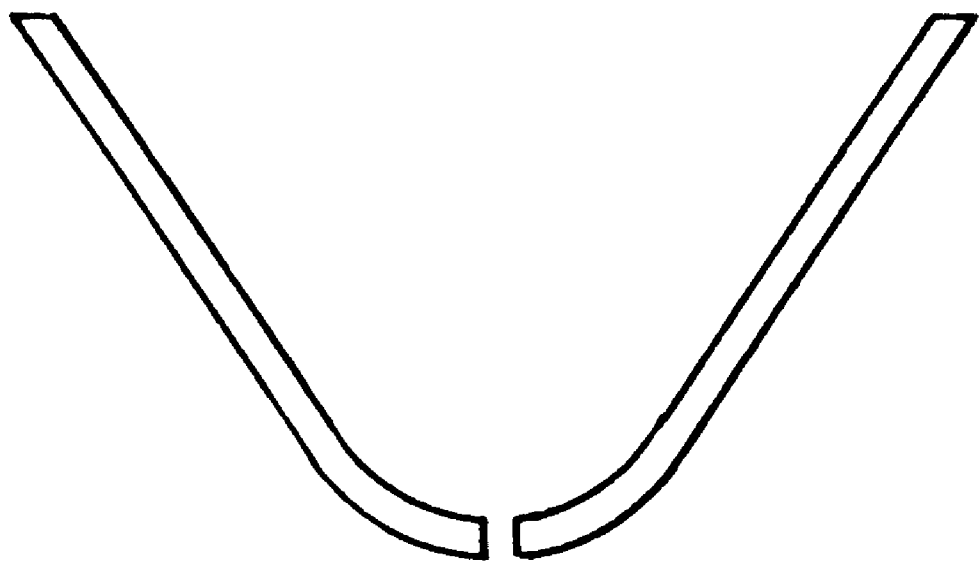
FIG. 1 is a drawing of a side view of a cradle used for the MIST Evaluation test.

"Disposable" includes being disposed of after usually a single use and not intended to be washed and reused.

"Front" and "back" are used throughout this description to designate relationships relative to the garment itself, rather than to suggest any position the garment assumes when it is positioned-on a wearer.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than 90° are designated "nonwettable" or hydrophobic.

"Inward" and "outward" refer to positions relative to the center of an absorbent garment, and particularly transversely and/or longitudinally closer to or away from the longitudinal and transverse center of the absorbent garment.

"Layer" when used in the singular can have the dual meaning of a single element or a plurality of elements.

"Liquid" means a nongaseous substance and/or material that flows and can assume the interior shape of a container into which it is poured or placed.

"Liquid communication" means that liquid such as urine is able to travel from one location to another location.

"Longitudinal" and "transverse" have their customary meanings. The longitudinal axis lies in the plane of the article when laid flat and fully extended and is generally parallel to a vertical plane that bisects a standing wearer into left and right body halves when the article is worm. The transverse axis lies in the plane of the article generally perpendicular to the longitudinal axis.

"Particles" refers to any geometric form such as, but not limited to, spherical grains, cylindrical fibers or strands, or the like.

"Spray" and variations thereof include forcefully ejecting liquid, either as a stream such as swirl filaments, or atomized particles through an orifice, nozzle, or the like, by means of an applied pressure of air or other gas, by force of gravity, or by centrifugal force. The spray can be continuous or non-continuous.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. Nos. 5,277,976 to Hogle et al., U.S. Pat. No. 5,466,410 to Hills and 5,069,970 and 5,057,368 to Largman et al., which describe fibers with unconventional shapes.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

As used herein, the term "coform" means a process in which at least one meltblown diehead is arranged near a chute through which other materials are added to the web while it is forming. Such other materials may be pulp, superabsorbent particles, cellulose or staple fibers, for example. Coform processes are shown in commonly assigned U.S. Pat. Nos. 4,818,464 to Lau and 4,100,324 to Anderson et al. Webs produced by the coform process are generally referred to as coform materials.

"Conjugate fibers" refers to fibers which have been formed from at least two polymer sources extruded from separate extruders but spun together to form one fiber. Conjugate fibers are also sometimes referred to as multicomponent bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. Nos. 5,277,976 to Hogle et al., and 5,069,970 and 5,057,368 to Largman et al., hereby incorporated by reference in their entirety, which describe fibers with unconventional shapes.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Bonded carded web" refers to webs that are made from staple fibers which are sent through a combing or carding unit, which separates or breaks apart and aligns the staple fibers in the machine direction to form a generally machine direction-oriented fibrous nonwoven web. Such fibers are usually purchased in bales which are placed in an opener/blender or picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

"Airlaying" is a well known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

"Personal care product" means diapers, training pants, absorbent underpants, adult incontinence products, and feminine hygiene products.

TEST METHODS

Figure 2:
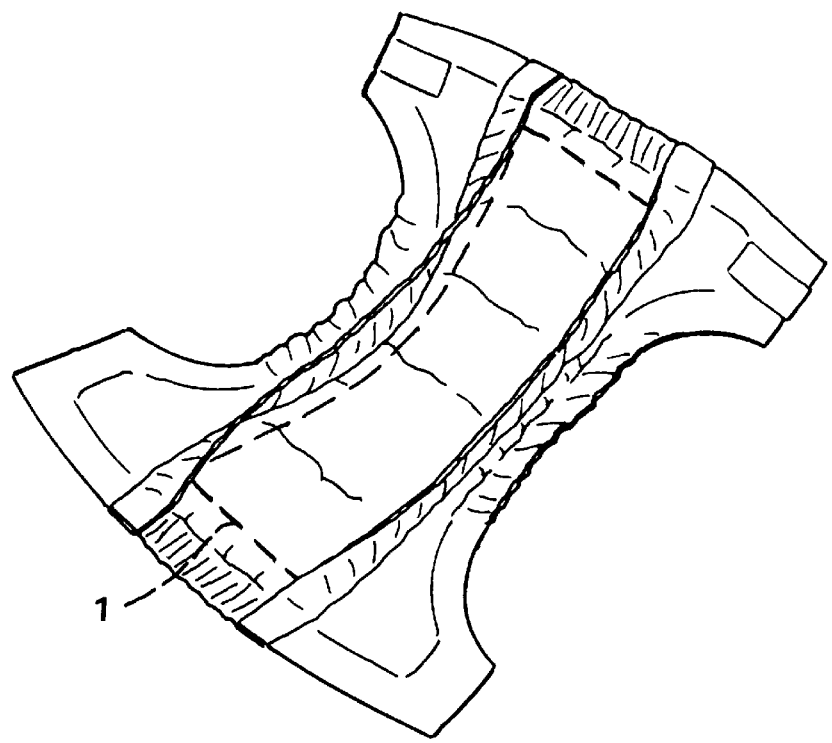
FIG. 2 is a drawing of a typical diaper having a surge layer 1 depicted by dashed lines.
Figure 3:
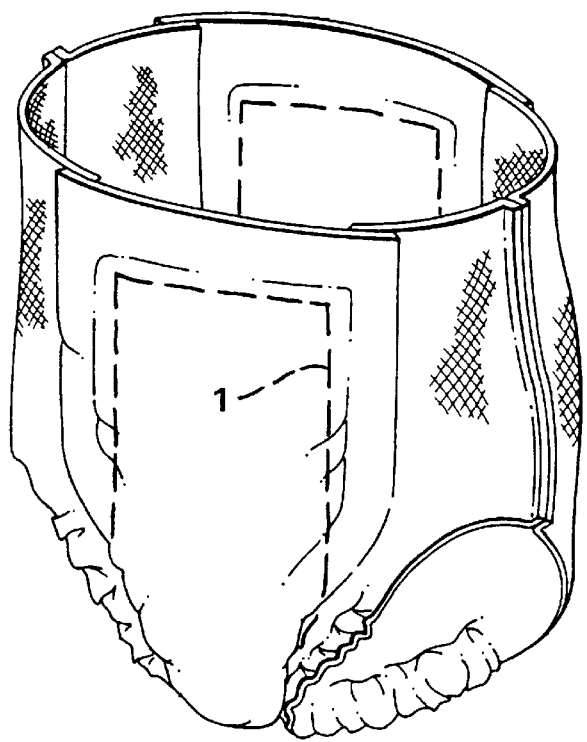
FIG. 3 is a drawing of a typical training pant having a surge layer 1 depicted by dashed lines.
Figure 4:
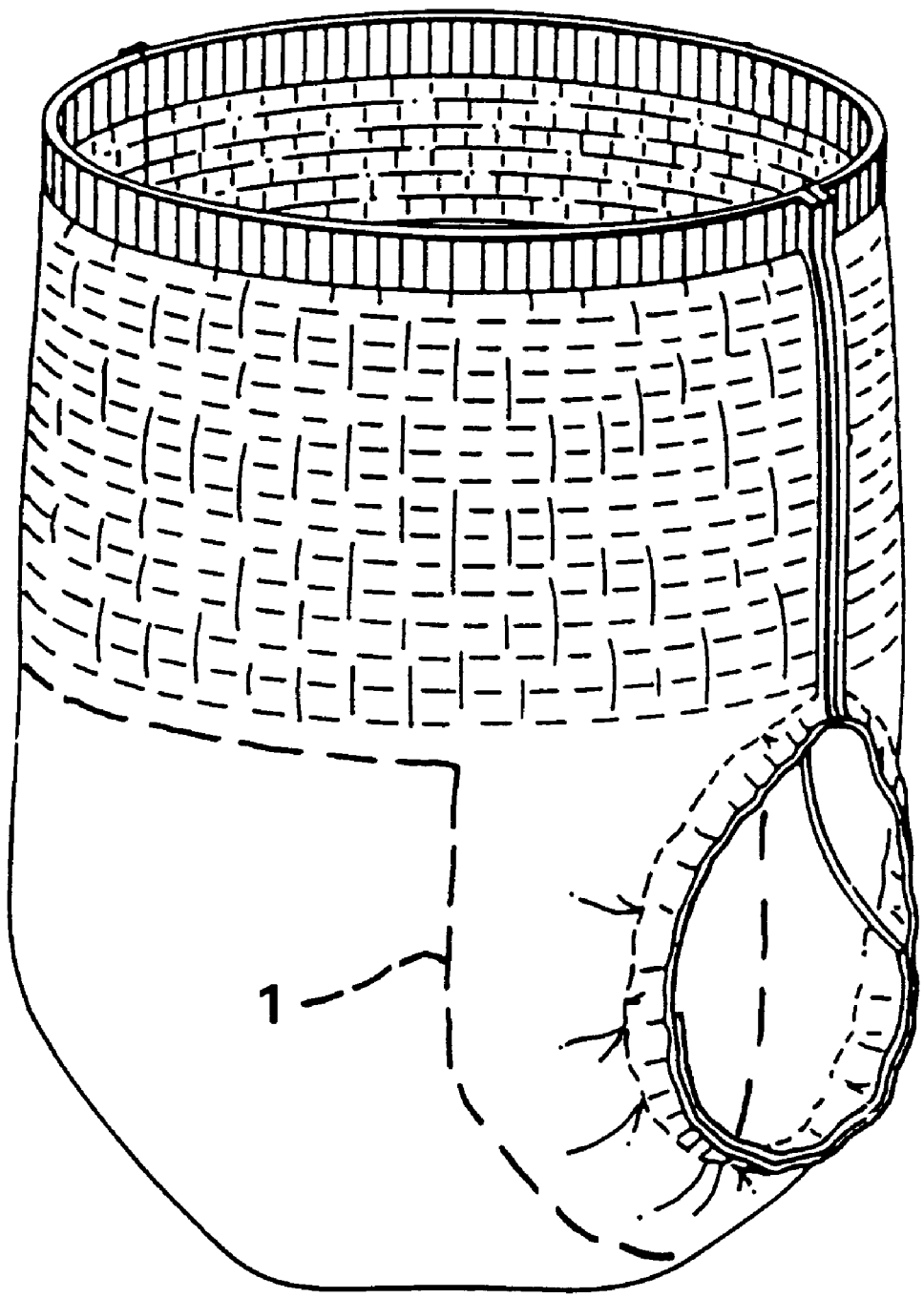
FIG. 4 is a drawing of a typical absorbent underpant having a surge layer 1 depicted by dashed lines.
Figure 5:
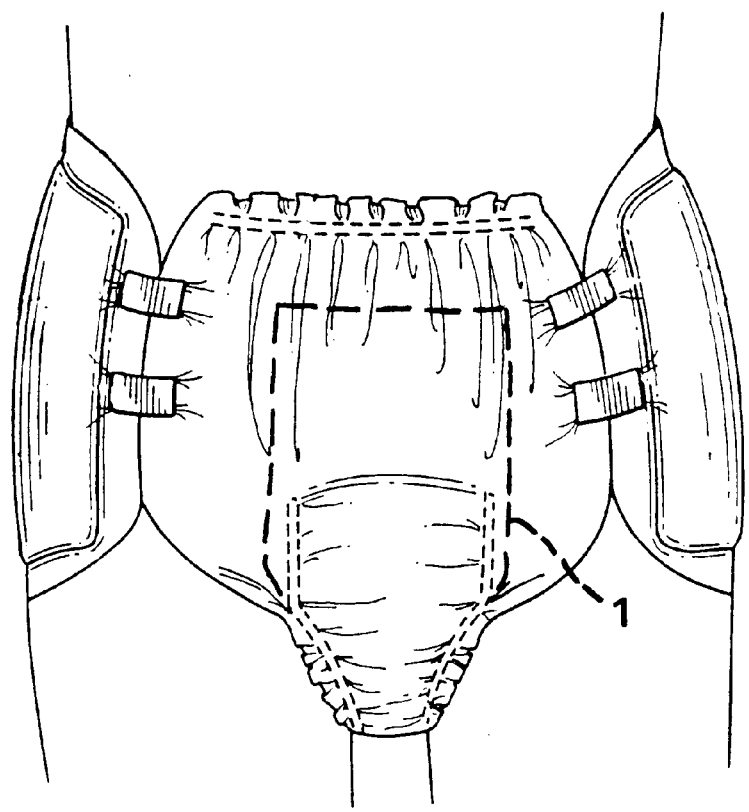
FIG. 5 is a drawing of a typical adult incontinence product having a surge layer 1 depicted by dashed lines.
Figure 6:
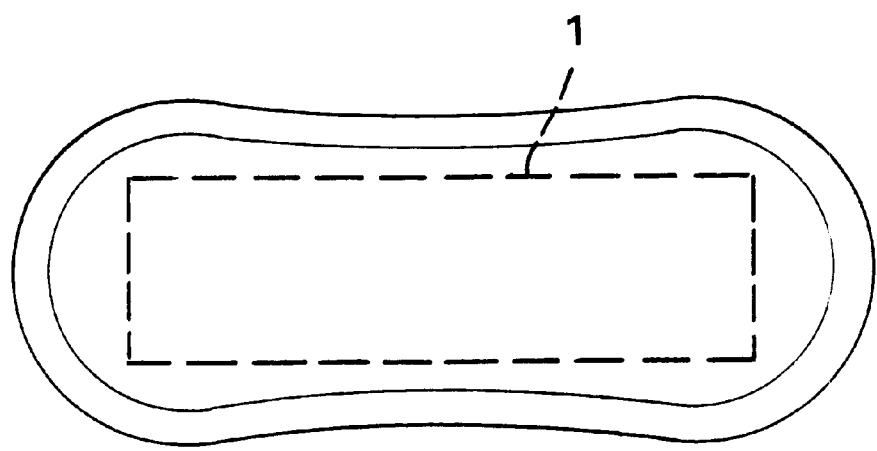
FIG. 6 is a drawing of a typical feminine hygiene product having a surge layer 1 depicted by dashed lines.

Multiple Insult Test (MIST Evaluation): In this test a fabric, material or structure composed of two or more materials is placed in an acrylic cradle to simulate body curvature of a user such as an infant. Such a cradle is illustrated in FIG. 2. The cradle has a width into the page of the drawing as shown of 33 cm and the ends are blocked, a height of 19 cm, an inner distance between the upper arms of 30.5 cm and an angle between the upper arms of 60 degrees. The cradle has a 6.5 mm wide slot at the lowest point running the length of the cradle into the page.

The material to be tested is placed on a piece of polyethylene film the same size as the sample and placed in the cradle. The material to be tested is insulted with 100 ml of a saline solution of 8.5 grams of sodium chloride per liter, at a rate of 20 cc/sec with a nozzle normal to the center of the material and ¼ inch (6.4 mm) above the material. The amount of runoff is recorded. The material is immediately removed from the cradle, weighed, and placed on a dry 40/60 pulp/superabsorbent pad having a density of 0.2 g/cc in a horizontal position under 0.01 psi pressure and weighed after 5, 15 and 30 minutes to determine fluid desorption from the material into the superabsorbent pad as well as fluid retention in the material. The pulp fluff and superabsorbent used in this test is Kimberly-Clark's (Dallas Tex.) CR-2054 pulp and Stockhausen Company's (of Greensboro, N.C. 27406) FAVOR 870 superabsorbent though other comparable pulp and superabsorbents could be used provided they yield a desorption pad of 500 gsm and 0.2 g/cc which after immersion into saline solution under free-swell conditions for 5 minutes, retains at least 20 grams of saline solution per gram of desorption pad after being subjected to an air pressure differential, by vacuum suction for example, of about 0.5 psi (about 3.45 kPa) applied across the thickness of the pad for 5 minutes. If the tested piece is made of other components (e.g. is a laminate) the components or layers are separated and weighed to determine liquid partitioning between-them and then reassembled after each weighing and placed back onto the fluff/superabsorbent. This test is repeated using fresh desorption pads on each insult so that a total of three insults are introduced and fluid partitioning measured over 1.5 hours with 30 minutes between insults. Five tests of each sample material are recommended.

Permeability: Permeability (k) may be calculated from the Kozeny-Carman equation. This is a widely used method. References include an article by R. W. Hoyland and R. Field in the Journal Paper Technology and Industry, December 1976, p. 291–299 and *Porous Media Fluid Transport and Pore Structure* by F. A. L. Dullien, 1979, Academic Press, Inc. ISBN 0-12-223650-5.

| | Calculated Variable | Equation | Dimensions |
|---|---|---|---|
| Permeability | = k | $= \dfrac{\varepsilon^3}{KS_0^2(1-\varepsilon)^2} \dfrac{1}{9.87 \times 10^{-9}}$ = | Darcys |
| Kozeny Constant | = K | $= \dfrac{3.5\varepsilon^3}{(1-\varepsilon)^{0.5}}[1 + 57(1-\varepsilon)^3]$ = | dimensionless |
| Surface area per mass of the material | = $S_V$ | $= \sum_i \dfrac{x_i}{r_{i,\text{eff}} \rho_i}$ | cm²/g |

| Calculated Variable | | Equation | Dimensions |
|---|---|---|---|
| Mass weighted average component density | $= \rho_{avg}$ | $= \left(\sum_i \frac{x_i}{\rho_i}\right)^{-1}$ | g/cm³ |
| Surface area per solid volume of the material | $= S_0$ | $= S_V \rho_{avg}$ | cm⁻¹ |
| Porosity | $= \epsilon$ | $\epsilon = 1 - \sum_i x_i \frac{\rho_{web}}{\rho_i}$ | dimensionless |
| Effective fiber radius | $= r_{i,eff}$ | $= \frac{V_i}{SA_i}$ | cm |
| Density of web | $= \rho_{web}$ | $= \frac{BW}{10^3 \cdot t}$ | g/cm³ |
| for long cylinders | $r_{i,eff}$ | $= \frac{\frac{\pi d_i^2 L}{4}}{\pi d_i L} = \frac{d_i}{4 \times 10^4}$ | |
| for spheres | $r_{i,eff}$ | $= \frac{\frac{4}{3}\frac{\pi d_i^3}{8}}{\pi d_i^2} = \frac{d_i}{6 \times 10^4}$ | | where $d_i$=diameter of component i (microns)
 $\rho_i$=density of component i (g/cm³)
 $x_i$=mass fraction of component i in web
 BW=weight of sample/area (g/m³)
 t=thickness of sample (mm) under 0.05 psi (23.9dyne/cm²) or 2.39 Pascal (N/m²) load Permeability Example Calculation For a structure which contains 57% southern softwood pulp, 40% superabsorbent and 3% binder fiber, and has a basis weight of 617.58 g/m² and a bulk thickness of 5.97 mm at 0.05 psi the example permeability calculation follows.

The component properties are as follows (note shape is approximated):

| Component | Shape | Diameter $d_i$ (microns) | Density $\rho_1$ (g/cm³) | Mass Fraction $x_i$ |
|---|---|---|---|---|
| Southern softwood | Cylinder | 13.3 | 1.55 | 0.57 |
| Superabsorbent | Sphere | 1125 | 1.50 | 0.40 |
| Binder | Cylinder | 17.5 | 0.925 | 0.03 |

$$\rho_{web}(g/cm^3) = \frac{BW}{10^3 \cdot t}$$

$$\rho_{web}(g/cm^3) = \frac{617.58}{(5.97)10^3}$$

$$\rho_{web}(g/cm^3) = 0.1034$$

$$\varepsilon = 1 - \sum_i x_i \frac{\rho_{web}}{\rho_i}$$

$$\varepsilon = 1 - 0.57\frac{0.1034}{1.55} - 0.40\frac{0.1034}{1.49} - 0.03\frac{0.1034}{0.925}$$

$$\varepsilon = 0.9309$$

$$S_V(cm^2/g) = \sum_i \frac{x_i}{r_{i,eff}\rho_i}$$

$$S_V(cm^2/g) = \frac{0.57}{\left(\frac{13.3}{4 \times 10^4}\right) \times 1.55} + \frac{0.40}{\left(\frac{1125}{6 \times 10^4}\right) \times 1.49} + \frac{0.03}{\left(\frac{17.5}{4 \times 10^4}\right) \times .0925}$$

$$S_V(cm^2/g) = 1194$$

$$\rho_{avg}(g/cm^3) = \left(\sum_i \frac{x_i}{\rho_i}\right)^{-1}$$

$$\rho_{avg}(g/cm^3) = \left(\frac{0.57}{1.55} + \frac{0.40}{1.49} + \frac{0.03}{0.925}\right)^{-1}$$

$$\rho_{avg}(g/cm^3) = 1.496$$

$$S_0(cm^{-1}) = S_V \rho_{avg}$$

$$S_0(cm^{-1}) = 1194 \times 1.496$$

$$S_0(cm^{-1}) = 1786$$

$$K = \frac{3.5\varepsilon^3}{(1-\varepsilon)^{0.5}}[1 + 57(1-\varepsilon)^3]$$

$$K = \frac{3.5(0.9309)^3}{(1-0.9309)^{0.5}}[1 + 57(1-0.9309)^3]$$

$$K = 10.94$$

-continued $$k = \frac{\varepsilon^3}{KS_0^2(1-\varepsilon)^2} \frac{1}{9.87 \times 10^{-9}}$$

$$k = \frac{(0.9309)^3}{(10.94)(1786)^2(1-0.9309)^2} \frac{1}{9.87 \times 10^{-9}}$$

$$k = 491 \text{ darcys}$$

Material caliper (thickness) The caliper of a material is a measure of thickness and is measured at 0.05 psi with a Starret-type bulk tester, in units of millimeters.

Density The density of the materials is calculated by dividing the weight per unit area of a sample in grams per square meter (gsm) by the bulk of the sample in millimeters (mm) at 68.9 Pascals and multiplying the result by 0.001 to convert the value to grams per cubic centimeter (g/cc). A total of three samples would be evaluated and averaged for the density values.

Wicking Time and Vertical Liquid Flux of an Absorbent Structure A sample strip of material approximately 2 inches (5 cm) by 15 inches (38 cm) is placed vertically such that when the sample strip is positioned above a liquid reservoir at the beginning of the test, the bottom of the sample strip will just touch the liquid surface. The liquid used was a 8.5 g/l saline solution. The relative humidity should be maintained at about 90 to about 98 percent during the evaluation. The sample strip is placed above the known weight and volume of liquid and a stopwatch started as soon as the bottom edge of the sample strip touches the surface of the solution.

The vertical distance of the liquid front traveling up the sample strip and the liquid weight absorbed by the sample strip at various times is recorded. The time versus liquid front height is plotted to determine the Wicking Time at about 5 centimeters and at about 15 centimeters. The weight of the liquid absorbed by the sample strip from the beginning of the evaluation to about 5 centimeters and to about 15 centimeters height is also determined from the data. The Vertical Liquid Flux value of the sample strip at a particular height was calculated by dividing the grams of liquid absorbed by the sample strip by each of: the basis weight (gsm), of the sample strip; the time, in minutes, needed by the liquid to reach the particular height; and the width, in inches, of the sample strip. Capillary tension in materials not containing superabsorbents (e.g. surge materials) is measured simply by the equilibrium vertical wicking height of a 8.5/l saline solution after 30 minutes.

DETAILED DESCRIPTION

Traditional absorbent systems for personal care products may be generalized as having the functions of surge control and containment (retention) or SC.

Surge control materials, the "S" in SC, are provided to quickly accept the incoming insult and either absorb, hold, channel or otherwise manage the liquid so that it does not leak outside the article. The surge layer may also be referred to as an intake layer, transfer layer, transport layer and the like. A surge material must typically be capable of handling an incoming insult of between about 60 and 100 cc at an insult volumetric flow rate of from about 5 to 20 cc/sec, for infants, for example.

Containment or retention materials, the "C" in SC, must absorb the insult quickly and efficiently. They should be capable of pulling the liquid from the distribution layer and absorbing the liquid without significant "gel blocking" or blocking of penetration of liquid further into the absorbent by the expansion of the outer layers of absorbent. Retention materials often contain high rate superabsorbent materials such as blends of polyacrylate superabsorbent and fluff. These materials rapidly absorb and hold liquid.

As mentioned above, traditional absorbent systems having the functions of surge control and containment usually hold the vast majority of any insult in the target area, usually the crotch. This results in personal care products having crotches which are quite wide. Examples of the holding ability and location of containment of various commercial diapers is presented in Table 3 of U.S. patent application Ser. No. 08/755,136, filed the same day and assigned to the same assignee as this application and entitled ABSORBENT ARTICLES WITH CONTROLLABLE FILL PATTERNS.

In contrast with traditional absorbent systems, the patent application ABSORBENT ARTICLES WITH CONTROLLABLE FILL PATTERNS presents an absorbent system which includes components that have been designed, arranged, and assembled so that within a certain time after each insult, liquid will be located in a pre-specified area of the absorbent system, i.e. remote from the target area. Using an absorbent system arbitrarily divided into five zones, these absorbent systems have a "fill ratio" of grams of fluid located in the center target zone, usually in the crotch, to each of the two end zones which is less than 5:1 after each of three insults of, 100 ml separated by 30 minutes. It is preferred that this fill ratio be less than 3:1, and most preferred to be less than 2.5:1. Many currently available commercial diapers have fill ratios of 20:1, 50:1 or even greater, i.e. they hold most insult liquid in the crotch.

In addition to the surge control and containment materials in traditional absorbent systems, recent work has introduced another layer that interacts with and may be interposed between the S and C layers. This new layer is a distribution layer, producing a system with surge control, distribution and containment or "SDC".

Distribution materials, the "D" in SDC, must be capable of moving fluid from the point of initial deposition to where storage is desired. Distribution must take place at an acceptable rate such that the target insult area, generally the crotch area, is ready for the next insult. By "ready for the next insult" it is meant that sufficient liquid has been moved out of the target zone so that the next insult results in liquid absorption and runoff within acceptable volumes. The time between insults can range from just a few minutes to hours, generally depending on the age of the wearer.

Absorbent products such as, for example, diapers, generally also have a liner which goes against the wearer, a backsheet which is the most exterior layer. An absorbent product may also contain other layers such as the multifunctional materials described in U.S. Pat. No. 5,843,063, filed the same day and assigned to the same assignee as this application and entitled MULTIFUNCTIONAL ABSORBENT MATERIALS AND PRODUCTS MADE THEREFROM. While it may appear obvious, it should be noted that in order to function effectively, the materials used in personal care product absorbent systems must have sufficient contact to transfer liquid between them.

The liner is sometimes referred to as a bodyside liner or topsheet and is adjacent the surge material. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating.

Various materials can be used in forming the bodyside liner of the present invention, including apertured plastic films, woven fabrics, nonwoven webs, porous foams, reticulated foams and the like. Nonwoven materials have been found particularly suitable for use in forming the bodyside liner, including spunbond or meltblown webs of polyolefin, polyester, polyamide (or other like fiber forming polymer) filaments, or bonded carded webs of natural polymers (for example, rayon or cotton fibers) and/or synthetic polymers (for example, polypropylene or polyester) fibers. For example, the bodyside liner can be a nonwoven spunbond web of synthetic polypropylene filaments having an average fiber size (from a sample of at least 10) ranging from about 12 to about 48 microns, and more particularly from about 18 to about 43 microns. The nonwoven web can have a basis weight (for example, ranging from about 10.0 grams per square meter (gsm) to about 68.0 gsm, and more particularly from about 14.0 gsm to about 42.0 gsm, a bulk or thickness ranging from about 0.13 millimeter (mm) to about 1.0 mm, and more particularly from about 0.18 mm to about 0.55 mm, and a density between about 0.025 grams per cubic centimeter (g/cc) and about 0.12 g/cc, and more particularly between about 0.068 g/cc and about 0.083 g/cc. Additionally, the permeability of such nonwoven web can be from about 150 Darcy to about 5000 Darcy. The nonwoven web can be surface treated with a selected amount of surfactant, such as about 0.28% Triton X-102 surfactant, or otherwise processed to impart the desired level of wettability and hydrophilicity. If a surfactant is used, it can be an internal additive or applied to the web by any conventional means, such as spraying, printing, dipping, brush coating and the like.

The surge layer is most typically interposed between and in intimate, liquid communicating contact with the bodyside liner and another layer such as a distribution or retention layer. The surge layer is generally subjacent the inner (unexposed) surface of bodyside liner. To further enhance liquid transfer, it can be desirable to attach the upper and/or lower surfaces of the surge layer to the liner and the distribution layer, respectively. Suitable conventional attachment techniques may be utilized, including without limitation, adhesive bonding (using water-based, solvent-based and thermally activated adhesives), thermal bonding, ultrasonic bonding, needling and pin aperturing, as well as combinations of the foregoing or other appropriate attachment methods. If, for example, the surge layer is adhesively bonded to the bodyside liner, the amount of adhesive add-on should be sufficient to provide the desired level(s) of bonding, without excessively restricting the flow of liquid from the liner into the surge layer. The surge material of this invention will be discussed in greater detail below.

As described in the previously cited, co-owned patent application MULTIFUNCTIONAL ABSORBENT MATERIALS AND PRODUCTS MADE THEREFROM, the multifunctional material has been designed to assist surge materials 1) by accepting a portion of the insult volume during forced flow, i.e. during an actual insult, 2) by desorbing the surge material of liquid during and after insults, 3) by allowing a portion of the insult volume to pass through itself (the multifunctional material) to the distribution material and 4) by permanently absorbing a portion of the liquid insult. If such a multifunctional material is used, the multifunctional material and surge should be designed to function together as described in previously cited, co-owned patent application MULTIFUNCTIONAL ABSORBENT MATERIALS AND PRODUCTS MADE THEREFROM. The basic structure of the multifunctional material is a unique blend of superabsorbent material, high bulk wet resilient pulp, and a structure stabilizing component such as a polyolefin binder fiber. The multifunctional material has a permeability of between about 100 and 10000 Darcys, a capillary tension between about 2 and 15 cm, and a runoff rate of less than 25 ml per 100 ml insult, over its life. The "life" of the multifunctional material is considered to be three insults of 100 ml each where each insult is separated by 30 minutes. In order to achieve the required capillary tension and permeability, its preferred that the multifunctional material have between 30 and 75 weight percent of slow rate superabsorbent, between 25 and 70 weight percent of pulp and from a positive amount up to about 10 percent of a binder component. The material should have a density between about 0.05 and 0.5 g/cc. The basis weight of the material will vary depending on the product application but should generally be between about 200 and 700 gsm. The multifunctional material is preferably located between the surge and distribution layers.

The distribution layer must be capable of moving fluid from the point of initial deposition to where storage is desired. Distribution must take place at an acceptable rate such that the target insult area, generally the crotch area, is ready for the next insult. The time between insults can range from just a few minutes to hours, generally depending on the age of the wearer. In order to achieve this transportation function, a distribution layer must have a high capillary tension value. Capillary tension in distribution materials is measured simply by the equilibrium wicking of a 8.5 g/ml saline solution according to the Vertical Liquid Flux rate test, not by the test method given for materials containing superabsorbents. A successful distribution layer must have a capillary tension greater than the adjacent layer (on the side toward the wearer) and preferably a capillary tension of at least about 15 cm. Because of the generally inverse relationship between capillary tension and permeability, such a high capillary tension indicates that the distribution layer will usually have a low permeability.

Another liquid transport property desired of a suitable distribution material is that it exhibit a Vertical Liquid Flux rate, at a height of about 15 centimeters, suitably of at least about 0.002 grams of liquid per minute per square meter (gsm) of distribution material per inch of cross-sectional width of the distribution material g/(min*gsm*inch), up to about 0.1 g/(min*gsm*inch). As used herein, the Vertical Liquid Flux rate value of a distribution material is meant to represent the amount of liquid transported across a boundary a specified vertical distance away from a centralized liquid insult location per minute per normalized quantity of the distribution material. The Vertical Liquid Flux rate, at a height of about 15 centimeters, of a distribution may be measured according to the test method described herein.

Another liquid transport property desired of a distribution material is that it exhibit a Vertical Liquid Flux rate, at a height of about 5 centimeters, suitably of at least about 0.01 g/(min*gsm*inch) up to about 0.5 g/(min*gsm*inch). The Vertical Liquid Flux rate, at a height of about 5 centimeters, of an absorbent structure may be measured according to the test method described herein.

Materials from which the distribution layer may be made include woven fabrics and nonwoven webs, foams and filamentious materials. For example, the distribution layer may be a nonwoven fabric layer composed of a meltblown or spunbond web of polyolefin, polyester, polyamide (or other web forming polymer) filaments. Such nonwoven fabric layers may include conjugate, biconstituent and homopolymer fibers of staple or other lengths and mixtures of such fibers with other types of fibers. The distribution layer also can be a bonded carded web, an airlaid web or a wetlaid pulp structure composed of natural and/or synthetic fibers, or a combination thereof. The distribution layer may have a basis weight of from 35 to 300 gsm, or more preferably from 80 to 200 gsm, a density of between about 0.1 and 0.5 g/cc and a permeability between about 50 and 1000 Darcys.

Retention materials are typically cellulosic materials or superabsorbents or mixtures thereof. Such materials are usually designed to quickly absorb liquids and hold them without, usually without release. Superabsorbents are commercially available from a number of manufactures including The Dow Chemical Company of Midland, Mich. and Stockhausen Gmbh. As described in the previously cited, co-owned patent application entitled ABSORBENT ARTICLES WITH CONTROLLABLE FILL PATTERNS, retention materials may be zoned and their composition chosen to move liquids away from the target zone to more remote storage locations. Such a design more efficiently uses the entire absorbent article, and in the case of a diaper, for example, helps allows for the production of a more narrow crotch item. The fill patterns and materials taught in ABSORBENT ARTICLES WITH CONTROLLABLE FILL PATTERNS result in liquid by weight in the target zone of less than 5 times that in the remote storage locations after single or multiple (up to three) 100 ml insults, a significant improvement over prior designs.

The backsheet is sometimes referred to as the outer cover and is the farthest layer from the wearer. The outer cover is typically formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting the diaper. The outer cover may be, for example, a polyethylene film having an initial thickness of from about 0.5 mil (0.012 millimeter) to about 5.0 mil (0.12 millimeter). The polymer film outer cover may be embossed and/or matte finished to provide a more aesthetically pleasing appearance. Other alternative constructions for outer cover include woven or nonwoven fibrous webs that have been constructed or treated to impart the desired level of liquid impermeability, or laminates formed of a woven or nonwoven fabric and thermoplastic film. The outer cover may optionally be composed of a vapor or gas permeable, microporous "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability. Backings may also serve the function of a mating member for mechanical fasteners, in the case, for example, where a nonwoven fabric is the outer surface.

In regard to surge materials, various woven fabrics and nonwoven webs can be used to construct a surge layer. For example, the surge layer may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The surge layer also can be a bonded carded web or an airlaid web composed of natural and/or synthetic fibers. The bonded carded web may, for example, be a powder bonded carded web, an infrared bonded carded web, or a through-air bonded carded web. The bonded carded webs can optionally include a mixture or blend of different fibers, and the fiber lengths within a selected web may range from about 3 mm to about 60 mm. Previous surge layers have had have a basis weight of at least about 0.50 ounce per square yard (about 17 grams per square meter), a density of at least about 0.010 gram per cubic centimeter at a pressure of 68.9 Pascals, a bulk of at least about 1.0 mm at a pressure of 68.9 Pascals, a bulk recovery of at least about 75 percent, a permeability of about 500 to about 5000 Darcy, and a surface area per void volume of at least about 20 square centimeters per cubic centimeter. Examples of surge materials may be found in U.S. Pat. No. 5,490,846 to Ellis et al. And in U.S. Pat. No. 5,364,382 to Latimer. Surge layers may be composed of a substantially hydrophobic material, and the hydrophobic material may optionally be treated with a surfactant or otherwise processed to impart a desired level of wettability and hydrophilicity. Surge layers can have a generally uniform thickness and cross-sectional area.

The surge material of this invention is designed to address a number of critical aspects of liquid intake and control. These critical aspects include the surge material permeability, capillary tension, pore structure, uniformity, and resilience.

The surge material structures of this invention must have permeability levels from 250–1500 Darcys across the life of the product to allow rapid liquid intake for multiple insults. In combination with the permeability range, the surge material must have a capillary tension level of 1.5–5 cm. This capillary tension range provides high control over liquid within the surge material that would otherwise spread uncontrollably as the user moves, causing leakage, particularly in narrow crotch width designs. When referring to diapers and training pants, a narrow crotch is one which is at most 7.6 cm in width, more particularly, at most 5 cm in width.

The capillary tension target range is achieved by incorporating wettable fibers such as cellulosics or synthetics into a surge material web. The surge material may be a blend of such cellulosic or synthetic fibers or may be a homogeneous single fiber-type structure. The surge material web must be wettable but not every fiber must be wettable to the same degree. The inventors have found that it is beneficial if at least 10 weight percent of these cellulosic or synthetic fibers are highly wettable in that they should have less than a 50 degree durable contact angle with synthetic urine. Wettability may be achieved by internal addition or more commonly, treatment with a surfactant. Additionally, the range of fiber size in the surge material web goes from subdenier (0.5 denier or about 6.8 microns) to 30 microns in diameter (about 6 denier) and more preferably the fiber size range is 9.6 microns to about 22 microns in diameter. The web density must be relatively low in the inventive surge material, preferably ranging from about 0.02 g/cc to about 0.07 g/cc.

The combination of fine denier and low density provide high fiber surface area for very high control over liquid movement. This combination will also result in pores within this type of structure which are highly connected. This means that fluid can move along the fine fibers to access the void volume provided by the pores within the structure. The fine fibers create pores that can trap and hold liquid for improved liquid control compared to structures in the prior art. However, because the pores are highly connected, the tightly held and controlled liquid can still desorb quite completely to underlying retention (or other) materials.

In yet another aspect of this invention, the fibers that form the surge material of this invention should be uniformly dispersed throughout. Uniformly dispersed fibers are desired to assure that the desired properties of capillary tension and permeability are present throughout the bulk of the structure. Uniformity is also important to ensure the connectivity potential of pores generated by the specified fiber range and density.

Finally, the resilience of the surge material helps maintain appropriate void volumes in order to intake and control incoming liquid insults that can exceed 100 ml and range from 30–150 ml over the life of the material. The "life of the material" as used herein is simulated by at least three insults of 100 ml each which are separated from each other by 30 minutes, and "appropriate void volumes" means void volumes between about 30 and 150 ml. The resilient nature of these surge materials is provided by the bonding that occurs at the high number of cross points provided by low denier fibers.

A number of structures were tested in a multiple insult test that utilized an acrylic cradle that is curved to simulate body curvature of real users such as infants who wear disposable diapers according to the MIST evaluation test. The results are given in Table 1 where the sample dimensions are in inches, n refers to the number of times the structure was tested, runoff after each of three insults is given in milliliters, and fluid retained is given in grams of fluid per gram of material tested. The structures are placed in the cradle in a symmetric fashion so that the insult is introduced to the middle of the sample. The insult volume is 100 ml and is introduced at 20 ml/sec. The amount of run-off is recorded, then the sample is removed from the cradle and placed on an absorbent retention structure for 5 minutes under 0.01 psi. The absorbent structure is a 40/60 blend of fluff and superabsorbent gel. After the 30 minutes the surge material is placed back into the cradle and reinsulted and runoff is recorded. The insult procedure is repeated 3 times to simulate a real environment multiple insult situation. Examples 1–8 are 4" (11 cm) wide by 8" (23 cm) long samples layered to provide 100 ml of void volume. Examples 9–11 are 2" (5 cm) wide by 6" (17 cm) long samples layered to provide 100 ml of accessible void volume. Note that the test samples contained approximately 150 cc of total volume calculated by multiplying length times width times thickness. The test configuration, however, resulted in less than 10.2 cm of the total length accessible and usable to the insults resulting in approximately 100 cc of accessible void volume. It has been empirically found that samples in the MIST test cradle use about 2 inches of length on either side of the point of insult, or 4 inches (10.2 cm), not the entire sample length, which results in the calculated 100 cc of void volume.

While Table 1 illustrates the functional data for examples that fall within the scope of the invention, Table 2 illustrates the compositional structural data for the same examples. The webs in Table 2 were all through air bonded. The denier, weight percentage and type of fiber are given under the headings "Fiber 1" and "Fiber 2" and the properties are in the labeled columns in the units shown. While the examples only include bonded carded web and airlaid technologies, other technologies can provide the structural features that cause the desired functional behavior. Note that all of the bonded carded webs used fibers from BASF Fibers, 6805 Morrison Boulevard, Charlotte, N.C. 28211-3577 which were bicomponent sheath/core polyethylene/polyethylene terephthalate (PE/PET) fibers with a polyethylene glycol based C S-2 finish as Fiber 1. All of the airlaid materials used binder fibers from Hercules Inc. Fibers Division, 7107 Alcovy Rd, Covington, Ga. 30209-2508 which were short cut bicomponent sheath/core polyethylene/polypropylene (PE/PP) fibers of Type T425 as Fiber 1. The rayon fibers were 1.5 denier Merge 18453 fibers from Courtaulds Fibers Incorporated of Axis, Ala. The fluff was CR 1654 pulp, commercially available from the Kimberly-Clark Corporation of Dallas, Tex. and is a predominately southern softwood roll pulp.

For the surge material of this invention, the first insult run-off value should be equal to or less than 30 ml from a 100 ml insult delivered at 20 ml/second, with the remaining two insults being equal to or less than 45 ml each. In the most preferred embodiments, all three insults have run-off values less than or equal to 25 ml.

In the examples that follow the component properties used in the calculations herein were as follows:

|  | Approximate shape | Denier | Density (g/cc) | Diameter (microns) |
|---|---|---|---|---|
| 1.5 denier rayon | Cylinder | 1.5 | 1.550 | 11.70 |
| 1.8 denier BASF PE/PET | Cylinder | 1.8 | 1.165 | 14.78 |
| 3 denier BASF PE/PET | Cylinder | 3 | 1.165 | 19.09 |
| 10 denier BASF PE/PET | Cylinder | 10 | 1.165 | 34.85 |
| 3 denier PE/PP | Cylinder | 3 | 0.930 | 21.36 |
| 6 denier PE/PP | Cylinder | 6 | 0.930 | 30.21 |
| 6 denier PET | Cylinder | 6 | 1.380 | 24.80 |
| 6 denier PP | Cylinder | 6 | 0.910 | 30.54 |
| CR0054 | Cylinder | #N/A | 1.550 | 13.30 |
| CR1654 | Cylinder | #N/A | 1.550 | 13.30 |
| CR2054 | Cylinder | #N/A | 1.550 | 13.30 |

| Polymer | Density (g/cc) |
|---|---|
| PET | 1.38 |
| PE | 0.95 |
| PP | 0.91 |
| Cellulose | 1.55 |
| Rayon | 1.55 |
| Hydrofil nylon | 1.14 |
| Nylon | 1.14 |

Note that the relationship between denier and diameter is as follows: diameter (microns)=(denier/(pi×fiber density×9×$10^5$))$^{1/2}$×$10^4$.

EXAMPLES

Example 1 is a bonded carded web that illustrates a good balance of the desired properties. This structure contains 90% by weight 3 denier bicomponent 4.5 inch (11.3 cm) PE/PET sheath/core fibers. The durable wettable nature in this web is supplied by a cellulosic (1.5 denier rayon) present at 10% by weight. The capillary tension level is 1.7 cm. At this level the cellulosic does not significantly collapse upon being insulted so the desired structural properties are similar across all three insults and the desired fluid control properties are very consistent across the multiple insults. Additionally, because the two fibers present in this structure are 1.5 denier or 3 denier, the similar denier range keeps the pore size range similar throughout the structure resulting in a highly connected pore structure that is well desorbed below the most preferred range of 2 g/g. A well desorbed web prepares the structure for a subsequent insult by regenerating void volume.

Examples 2 and 3 are airlaid materials that incorporate higher levels of cellulose (70–80% by weight fluff) to provide the durable, wettable nature to the web. Initial structural properties and initial capillary tension levels are good and this is reflected in very low first run-off values, however, high cellulose content leads to significant wet collapse. Final properties and function are difficult to maintain because of the wet collapse and at 80% fluff Example 3, the material fails on the third insult. In-use deformation by a wearer would cause an even higher degree of collapse with such a high cellulosic content material and wetness levels would likely be higher than Example 1.

Examples 4 and 5 are bonded cared webs and illustrate a tendency to wet collapse and hold fluid as a low wet modulus component is increased in concentration. Example 4 contains 10% 1.5 denier rayon to provide wettability to the surge material while Example 5 contains 50% 1.5 denier rayon to provide this feature. Both have acceptable run off values, but the higher cellulosic containing web of Example 5 wet-collapses and so has much higher second and third run-offs.

In Example 6, the cellulose (fluff) content is 40% by weight, much lower than the 80% level in airlaid Examples 3. At this 40% level, with a 60% 6 denier synthetic component, run-off values are low and consistent from insult to insult, because web structural features are more consistently maintained. Example 6 illustrates the preferred balance of properties for airlaid technology.

Examples 7–9, are again bonded carded web materials, but unlike Example 1, these examples utilize 100% synthetics with wettable treatments to provide the wettable nature. These samples posses the specified capillary and permeability but are based on all synthetic fibers with topical treatment for wettability. Topical surface treatments with adequate durability can perform well in appropriate material structures of the present invention.

While all the material examples function well, the higher capillary tension, lower permeability structures provide the best performance in these examples. The functional data illustrates that the material structures of this invention can also provide run-off values for narrow crotch designs. Low permeability from higher density, however, results in potential intake restrictions at high void rates. Additionally at high density, higher mass is required to deliver adequate void volume. The most preferred structures to provide the lowest multiple insult run-offs, the best intake rate, and lowest mass for needed void volume, would incorporate the smallest diameter fibers (0.5 denier) with the most wettable surface ($\leq 30°$ contact angle with urine), and be the most uniform, stable structure at the pore level.

Technology and raw material deficiencies limit assembling the required structure for the optimum balance of intake performance properties, but this material can be defined and simulated by current mathematical modeling tools. The prophetic examples of Table 3 illustrate suitable structures from mathematical modeling tools which were developed by setting the fiber size, web density and contact angle limitations and calculating the other value to achieve the desired permeability. The prophetic examples may be calculated by using a permeability model like the Kozeny-Carmen equation which is known in the art Agreement between calculated and measured permeability may be seen by the data in Table 2 where Examples 1–6 have both measured and calculated permeabilities which agree fairly well. Once fiber size and web density have been identified, the contact angle required to achieve a desired capillary tension is calculated using, for example, the LaPlace equation, which is well known in the art.

Using the data of Table 3 and comparing prophetic example A to B, C to D, and E to F one can see the benefit of reducing fiber size and web density on the mass required to achieve a certain void volume level. It is important to point out that for a given fiber size reduction, the web density must also be reduced in order to maintain the desired permeability level. Comparing prophetic example A to C one can see that extra mass is required to provide void volume with a lower permeability structure when utilizing the same fiber size. Comparing prophetic examples B, D, G one can see that web density controls mass requirements to achieve void volume requirements. The benefit of using smaller fiber sizes is the ability to achieve lower permeability with the same mass of fibers.

Table 4 describes are Comparative Example materials that fall outside the scope of this invention. All were 4 inch by 8 inch samples. In Table 4, "formation tech" refers to the method of making the web where BCW means bonded-carded web, and meltblown and airlaid have their convential meanings. The density is given gm/cc, K is calculated permeability in Darcys, BW is basis weight in grams per square meter, and the runoff for three insults is given in ml. The first three examples in this table illustrate materials made according to U.S. Pat. No. 5,364,382.

Comparative Example 1 is a bonded carded web that blends low denier (1.5) cotton and high denier (40) PET fibers. This wide difference in fiber sizes creates intermixed pore sizes which interfere with pore connectivity within the structure. The large pores keep the capillary tension level low and outside of this invention even though a wettable component (cotton) is in the structure. Furthermore, the intermixed pore sizes cause local areas that have permeability levels above the average calculated and shown in Table 4. These areas in the web have very low control over the fluid. Low capillary tension and some areas of high permeability result in high run-off values, outside the scope of this invention.

Comparative Example 2 is also a bonded carded web that blends a wide range of fiber sizes. In this case capillary tension is low and permeability is high throughout the structure resulting in unacceptable, even higher run-off valves.

Comparative Example 3 is from a meltblown formation technology, again with a very wide range of fibers sizes as shown by the standard deviation, resulting in local areas of high permeability and therefore reduced control over the liquid.

The last four structures in Table 4 illustrate airlaid and bonded carded web materials that also fall outside of the scope of the invention.

Comparative Example 4, for example, has a starting capillary tension level that is above the desired 5 cm level and a permeability below the desired 250 Darcy limit. While these levels produce acceptable first insult run-off values, the high cellulose content in combination with the lower denier fibers cannot maintain performance. Wet collapse causes an increase in capillary tension and decrease in permeability resulting in high and unacceptable second and third insult run-off valves. Comparative Example 5 illustrates a similar mechanism of wet collapse with high second and third run-offs.

Comparative Example 6 is a bonded carded web structure that is near the limits of both capillary tension and permeability levels, but blends large and small fibers which results in the two properties not being uniformly maintained throughout the structure. While the difference in fiber sizes are not as large as Comparative Examples 1, 2 and 3, the difference is great enough to cause intermixed pores and inadequate liquid control.

Finally, Comparative Example 7 is an airlaid structure that utilizes very high cellulose content (80%). With this amount of fluff, initial functional performance is good, but wet collapse prevents good performance on second and third insults.

TABLE 1

| Example | Sample Dimensions | n = | Run-off (ml) 1 | 2 | 3 | Fluid Retained (g/g) 1 | 2 | 3 |
|---|---|---|---|---|---|---|---|---|
| 1 | 4 × 8 | 3 | 20 | 21 | 19 | 1.34 | 1.70 | 1.60 |
| 2 | 4 × 8 | 3 | 1 | 24 | 33 | 3.69 | 4.43 | 3.28 |
| 3 | 4 × 8 | 3 | 7 | 39 | 50 | 2.12 | 2.28 | 3.56 |
| 4 | 4 × 8 | 3 | 3 | 22 | 26 | 3.10 | 3.90 | 3.99 |
| 5 | 4 × 8 | 3 | 9 | 38 | 34 | 4.12 | 2.65 | 4.37 |
| 6 | 4 × 8 | 3 | 12 | 14 | 15 | 2.97 | 1.69 | 1.76 |
| 7 | 4 × 8 | 5 | 33 | 39 | 38 | 2.10 | 2.40 | 2.50 |
| 8 | 4 × 8 | 5 | 11 | 21 | 18 | 1.60 | 1.40 | 1.60 |
| 9 | 2 × 6 | 5 | 20 | 24 | 20 | 1.18 | 1.23 | 1.50 |
| 10 | 2 × 6 | 5 | 30 | 42 | 40 | 3.76 | 4.49 | 3.45 |
| 11 | 2 × 6 | 5 | 10 | 27 | 20 | 2.87 | 2.55 | 3.01 |

TABLE 2

| Example | Formation Technology | Fiber 1 | Fiber 2 | Web Density g/cc | Capillary Tension (cm) | Calculated Perm. Darcys | Measured Perm. Darcys | Basis Weight for 100 ml vv |
|---|---|---|---|---|---|---|---|---|
| 1 | Bonded Carded Web | 90% 3 denier BICO PE/PET | 10% 1.5 denier Rayon | 0.034 | 1.7 | 1247 | 1635 | 317 |
| 2 | Airlaid | 30% 3 denier BICO PE/PP | 70% fluff | 0.040 | 2.6 | 825 | 1177 | 551 |
| 3 | Airlaid | 20% 6 denier BICO PE/PP | 80% fluff | 0.035 | 3.8 | 1119 | 1127 | 406 |
| 4 | Bonded Carded Web | 90% 1.8 denier BICO/PE/PET | 10% 1.5 denier Rayon | 0.054 | 3.0 | 393 | 482 | 562 |
| 5 | Bonded Carded Web | 50% 1.8 denier BICO PE/PET | 50% 1.5 denier Rayon | 0.049 | 3.7 | 450 | 475 | 543 |
| 6 | Airlaid | 60% 6 denier BICO PE/PP | 40% fluff | 0.044 | 1.6 | 1117 | 1110 | 510 |
| 7 | Bonded Carded Web | 100% 1.8 denier BICO PE/PET | — | 0.029 | 1.5 | 1005 | | 639 |
| 8 | Bonded Carded Web | 100% 1.8 denier BICO PE/PET | — | 0.060 | 3.0 | 336 | | 1348 |
| 9 | Bonded Carded Web | 100% 3.0 denier BICO PE/PET | — | 0.059 | 2.2 | 574 | | 1348 |
| 10 | Bonded Carded Web | 100% 1.8 denier BICO PE/PET | — | 0.029 | 1.5 | 1005 | | 639 |
| 11 | Bonded Carded Web | 100% 1.8 denier BICO PE/PET | — | 0.060 | 3.0 | 336 | | 1348 |

TABLE 3

| Prophetic Ex. | Fiber Radius (microns) | Web Density (gm/cc) | Contact Angle (degrees) | Capillary Tension (cm) | Permeability (sq. micron) | Mass for 100 ml Void Volume (gm) |
|---|---|---|---|---|---|---|
| A | 13.9 | 0.05 | 57 | 2.5 | 1000 | 5.28 |
| B | 6.7 | 0.02 | 47 | 2.5 | 1000 | 2.04 |
| C | 14.0 | 0.06 | 63 | 2.5 | 750 | 6.42 |
| D | 5.8 | 0.02 | 54 | 2.5 | 750 | 2.04 |
| E | 13.1 | 0.07 | 69 | 2.5 | 500 | 7.58 |
| F | 6.5 | 0.03 | 64 | 2.5 | 500 | 3.1 |
| G | 4.8 | 0.02 | 61 | 2.5 | 500 | 2.04 |

TABLE 4

| Comp. Example | Formation Tech | Composition | Density | CT | K | BW | Run-off $1^{st}$ | Run-off $2^{nd}$ | Run-off $3^{rd}$ |
|---|---|---|---|---|---|---|---|---|---|
| 1 | BCW | 50% 40 denier PET<br>35% 1.5 denier Cotton<br>15% 1.5 denier PE/PP BICO | 0.027 | 1 | 2785 | 317 | 55 | 50 | 51 |
| 2 | BCW | 40% 40 denier PET<br>25% 3 denier Rayon<br>15% 6.5 denier PET<br>20% 6.0 denier PE/PP BICO | 0.050 | 1 | 8458 | 995 | 65 | 62 | 60 |
| 3 | Meltblown | Macrofiber Meltblown Hydrofil ® Fiber diameter mean 62.5 μm, Std Dev 40.9 μm | 0.083 | 5 | 3520 | 901 | 39 | 41 | 44 |
| 4 | Airlaid | 30% 1.8 denier PE/PP BICO<br>70% Pulp | 0.093 | 8.9 | 182 | 860 | 17 | 68 | 58 |
| 5 | Airlaid | 50% 1.8 denier PE/PP BICO<br>50% Pulp | 0.065 | 6.5 | 331 | 545 | 2 | 58 | 57 |
| 6 | BCW | 50% 10 denier PE/PET BICO<br>50% 1.5 denier Rayon | 0.028 | 1.5 | 2999 | 293 | 35 | 39 | 42 |
| 7 | Airlaid | 20% 6.0 denier PE/PP BICO<br>80% Pulp | 0.035 | 3.8 | 1119 | 406 | 7 | 39 | 50 |

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A personal care product selected from the group consisting of diapers, training pants, absorbent underpants, adult incontinence products and feminine hygiene products comprising a wettable web of fibers of at most 30 microns in diameter wherein said web has a permeability between about 250 and 1500 Darcys, a capillary tension between about 1.5 and 5 cm, and which maintains said permeability and capillary tension over said web life.

2. The product of claim 1 wherein said personal care product is a feminine hygiene product.

3. The product of claim 1 wherein said personal care product is an adult incontinence product.

4. The product of claim 1 wherein said personal care product is a diaper.

5. The diaper of claim 4 having a crotch width of at most 7.6 cm.

6. A personal care product selected from the group consisting of diapers, training pants, absorbent underpants, adult incontinence products and feminine hygiene products comprising a web having at least 10 weight percent of wettable fibers of at most 30 microns in diameter wherein said web is produced by a method selected from the group consisting of carding and bonding, and airlaying and wherein said web has a density of from about 0.02 g/cc to about 0.07 g/cc and a capillary tension between about 1.5 and 5 cm.

7. The product of claim 6 wherein said personal care product is a feminine hygiene product.

8. The product of claim 6 wherein said personal care product is an adult incontinence product.

9. The product of claim 6 wherein said personal care product is a diaper.

10. The diaper of claim 9 having a crotch width of at most 7.6 cm.

11. A surge material for personal care products comprising a web of from about 10 to 100 weight percent wettable fibers of at most 30 microns in diameter, wherein said web has a density of from about 0.02 g/cc to about 0.07 g/cc, a permeability between about 250 and 1500 Darcys, a capillary tension between about 1.5 and 5 cm, and which maintains said permeability and capillary tension through three insults of 100 ml each where each insult is separated by 30 minutes.

12. A personal care product selected from the group consisting of diapers, training pants, absorbent underpants, adult incontinence products and feminine hygiene products comprising the material of claim 11.

13. The product of claim 12 wherein said personal care product is a feminine hygiene product.

14. The product of claim 12 wherein said personal care product is an adult incontinence product.

15. The product of claim 12 wherein said personal care product is a diaper.

16. The diaper of claim 13 having a crotch width of at most 7.6 cm.

* * * * *